(12) United States Patent
Ben-Ezra et al.

(10) Patent No.: US 10,869,627 B2
(45) Date of Patent: Dec. 22, 2020

(54) SYSTEM AND METHOD FOR FUSING INFORMATION RELATED TO A DRIVER OF A VEHICLE

(71) Applicant: OSR Enterprises AG, Cham (CH)

(72) Inventors: Yosef Ben-Ezra, Petach Tikva (IL); Samuel Hazak, Holon (IL); Yaniv Ben-Haim, Kfar-Mordechai (IL); Shai Nissim, Tel Aviv (IL); Yoni Schiff, Yahod (IL)

(73) Assignee: OSR ENTERPRISES AG, Cham (CH)

( * ) Notice: Subject to any disclaimer, the term of this patent is extended or adjusted under 35 U.S.C. 154(b) by 0 days.

(21) Appl. No.: 15/642,323

(22) Filed: Jul. 5, 2017

(65) Prior Publication Data
US 2019/0008437 A1    Jan. 10, 2019

(51) Int. Cl.
| | |
|---|---|
| A61B 5/18 | (2006.01) |
| G06Q 40/08 | (2012.01) |
| G08B 21/18 | (2006.01) |
| G06K 9/00 | (2006.01) |
| G06K 9/62 | (2006.01) |
| G05D 1/00 | (2006.01) |
| B60W 50/00 | (2006.01) |
| B60W 50/14 | (2020.01) |
| A61B 5/00 | (2006.01) |
| A61B 5/1455 | (2006.01) |
| A61B 5/16 | (2006.01) |

(Continued)

(52) U.S. Cl.
CPC .............. *A61B 5/18* (2013.01); *A61B 5/0075* (2013.01); *A61B 5/14551* (2013.01); *A61B 5/165* (2013.01); *B60W 50/0098* (2013.01); *B60W 50/14* (2013.01); *G05D 1/0088* (2013.01); *G06K 9/00845* (2013.01); *G06K 9/2018* (2013.01); *G06K 9/6289* (2013.01); *G06Q 40/08* (2013.01); *G08B 21/06* (2013.01); *G08B 21/182* (2013.01); *B60W 2420/403* (2013.01); *B60W 2540/043* (2020.02); *B60W 2540/21* (2020.02); *B60W 2540/22* (2013.01); *B60W 2555/20* (2020.02); *B60W 2556/60* (2020.02); *G06K 9/00255* (2013.01); *G06K 9/00335* (2013.01)

(58) Field of Classification Search
CPC .... A61B 5/18; A61B 5/0075; B60W 50/0098; B60W 50/14; G05D 1/0088; G06K 9/00845; G06K 9/6289; G06Q 40/08; G08B 21/182
See application file for complete search history.

(56) References Cited

U.S. PATENT DOCUMENTS 5,835,008 A * 11/1998 Colemere, Jr. ........ B60Q 1/441
340/439
7,027,621 B1 * 4/2006 Prokoski ............ G06K 9/00248
180/272

(Continued)

*Primary Examiner* — Behrang Badii
*Assistant Examiner* — Daniel L Greene

(57) ABSTRACT

A method, apparatus and computer program product of determining a state of a vehicle driver, the method comprising: receiving an image of the driver captured by a hyper spectral camera capable of imaging body features invisible to a human; receiving telemetry information from a car telemetry system; analyzing the image to receive at least one indicator to a clinical parameter of the driver; and fusing the at least one indicator with the telemetry information to obtain an assessment to a stress level of the driver.

18 Claims, 2 Drawing Sheets

(51) Int. Cl.
*G06K 9/20* (2006.01)
*G08B 21/06* (2006.01)

(56) References Cited

U.S. PATENT DOCUMENTS

| | | | | |
|---|---|---|---|---|
| 2004/0209594 | A1* | 10/2004 | Naboulsi | B60R 11/0264 455/404.1 |
| 2008/0297336 | A1* | 12/2008 | Lee | B60H 1/00742 340/439 |
| 2011/0088374 | A1* | 4/2011 | Johnson | F01N 3/023 60/285 |
| 2011/0125477 | A1* | 5/2011 | Lightner | G05B 13/048 703/11 |
| 2011/0238647 | A1* | 9/2011 | Ingram | G08G 1/20 707/706 |
| 2014/0229060 | A1* | 8/2014 | MacNeille | G06F 17/00 701/36 |
| 2014/0376816 | A1* | 12/2014 | Lagae | G01N 15/1436 382/195 |
| 2015/0019094 | A1* | 1/2015 | Larkin | B60K 23/08 701/65 |
| 2015/0112606 | A1* | 4/2015 | He | G06F 21/00 702/19 |
| 2015/0164351 | A1* | 6/2015 | He | A61B 5/1171 702/19 |
| 2015/0271329 | A1* | 9/2015 | Deshmukh | G16H 40/67 379/265.06 |
| 2016/0354027 | A1* | 12/2016 | Benson | A61M 21/02 |
| 2017/0112671 | A1* | 4/2017 | Goldstein | A61B 5/6817 |
| 2017/0221149 | A1* | 8/2017 | Hsu-Hoffman | G06Q 40/08 |
| 2017/0305349 | A1* | 10/2017 | Naboulsi | B60R 1/04 |
| 2017/0327035 | A1* | 11/2017 | Keiser | B60Q 9/008 |
| 2017/0370732 | A1* | 12/2017 | Bender | G05D 1/0088 |

* cited by examiner

SYSTEM AND METHOD FOR FUSING INFORMATION RELATED TO A DRIVER OF A VEHICLE

TECHNICAL FIELD

The present disclosure relates to assessing the stress level of a driver and to utilizing this assessment for improving safety of the driver and the environment.

BACKGROUND

A driver of a vehicle carries enormous responsibility to the wellbeing of himself, passengers in the car, other people in the environment, and property, including the driver's vehicle and other vehicles and objects in the environment.

The driver's behavior also has effect on the behavior of other drivers. Aggressive behavior, including for example denying the right of way from other drivers, over speeding, tailgating, crossing lanes or other behaviors is not only dangerous in itself, but may also cause other drivers to react aggressively too, due to confusion, as vengeance or since they become aggravated too, while patient and courteous behavior may improve the atmosphere and the driving manners of other drivers in the vicinity.

The driving style of a driver is largely affected by the basic character of the driver, the driver's physical health which in itself may comprise a multiplicity of factors, the driver's mental health and mental status, including for example the current stress level experienced by the driver.

BRIEF SUMMARY

One exemplary embodiment of the disclosed subject matter is a computer-implemented method of determining a state of a vehicle driver, to be performed by a device comprising a processor and a memory device, the method comprising: receiving an image of the driver captured by a hyper spectral camera capable of imaging body features invisible to a human; receiving telemetry information from a car telemetry system; analyzing the image to receive an indicator to a clinical parameter of the driver; and fusing the indicator with the telemetry information to obtain an assessment to a stress level of the driver. The method can further comprise determining and taking an action in response to the stress level exceeding a predetermined threshold. Within the method, the action is optionally affecting a behavior of a car system. Within the method, the car system is optionally an autonomous driving system. Within the method, the behavior optionally relates to changing parameters in accordance with a weather condition and driver behavior. Within the method, the action is optionally collecting information to be provided to an insurer or making an offer to the driver. The method can further comprise collecting information related to a multiplicity of drivers in a road, and issuing an alert related to a road, subject to a multiplicity of drivers having stress levels exceeding a threshold. The method can further comprise: receiving data from an additional source; and analyzing the data to obtain an additional indicator; and fusing the additional indicator with the telemetry information and the indicator to obtain the assessment. Within the method, the additional source is optionally an image capture device or a voice capture device, and further comprising analyzing an image captured by the image capture device or voice captured by the voice capture device. Within the method, the additional source is at least one item selected from the group consisting of: a calendar of the driver, a global positioning system, a weather forecast source, a road condition report and a wearable device. The method can further comprise determining in accordance with the calendar and with a Global Positioning System whether the driver is late for a meeting. The method can further comprise adapting parameters or thresholds from a behavior of the driver over time; and using the parameters or thresholds as learned in obtaining a stress level assessment.

Another exemplary embodiment of the disclosed subject matter is an apparatus for fusing information related to a driver of a vehicle, the apparatus comprising: a hyper spectral camera capable of imaging body features invisible to a human; a car telemetry system providing telemetry information; a processor adapted to perform the steps of: receiving an image of the driver captured by the hyper spectral camera; receiving telemetry information from the car telemetry system; analyzing the image to receive an indicator to a clinical parameter of the driver; and fusing the indicator with the telemetry information to obtain an assessment to a stress level of the driver. Within the apparatus, the processor is optionally further adapted to determine and take an action in response to the stress level exceeding a predetermined threshold. Within the apparatus, the action is optionally affecting an autonomous driving system or an alert system. Within the apparatus, the action is optionally collecting information to be provided to an insurer or making an offer to the driver. Within the apparatus, the processor is optionally further adapted to: receive data from an additional source; analyze the data to obtain an additional indicator; and fuse the additional indicator with the telemetry information and the indicator to obtain the assessment. Within the apparatus, the additional source is optionally selected form the group consisting of: an image capture device, a voice capture device, a calendar of the driver, a global positioning system, a weather forecast source, a road condition report and a wearable device. Within the apparatus, the processor is optionally further adapted to: adapt parameters or thresholds from a behavior of the driver over time; and use the parameters or thresholds as learned in obtaining a stress level assessment.

Yet another exemplary embodiment of the disclosed subject matter is a computer program product comprising a non-transitory computer readable storage medium retaining program instructions configured to cause a processor to perform actions, which program instructions implement: receiving an image of the driver captured by the hyper spectral camera; receiving telemetry information from the car telemetry system; analyzing the image to receive an indicator to a clinical parameter of the driver; and fusing the indicator with the telemetry information to obtain an assessment to a stress level of the driver.

BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

DETAILED DESCRIPTION

Figure 1:
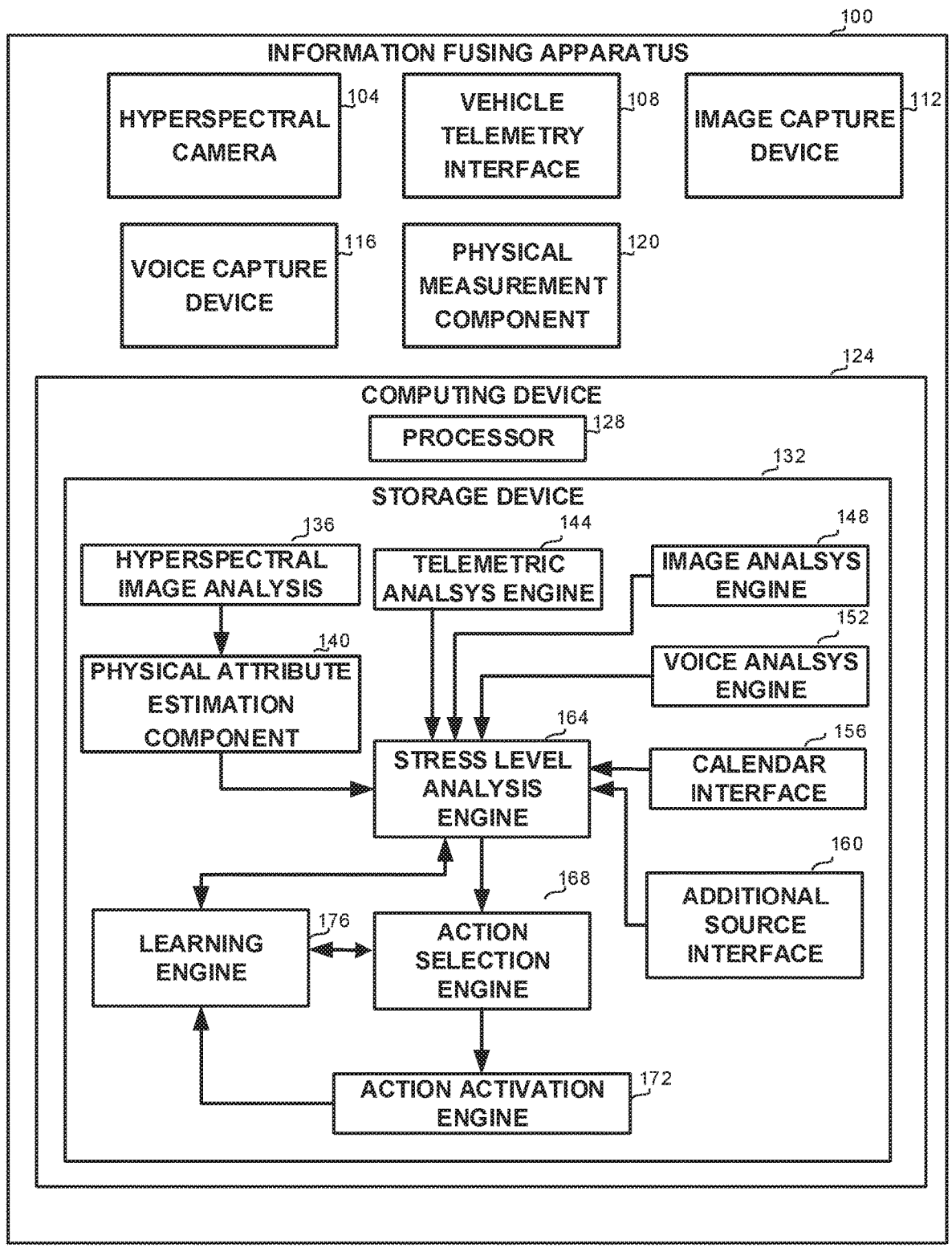
FIG. 1 is a schematic block diagram of an apparatus for assessing and utilizing the assessment of the stress level of a driver, in accordance with some embodiments of the disclosure.

Multi-spectral capturing is a technology that is gaining popularity and becoming more and more affordable. A multi spectral camera is a camera that captures images at two or more frequency bands across the electromagnetic spectrum. The wavelengths are separated by filters or other components that are sensitive to a particular wavelength.

Thus, a multi spectral camera provides images having features at two or more separate wavelength bands.

Common wavelengths captured by multi spectral cameras belong to the following ranges:

Visible blue (450-510 nanometers);
Visible Green (530-590 nanometers);
Visible Red (640-670 nanometers);
Red-Edge (705-745 nanometers);
Near Infrared 1 (760-900 nanometers);
Near Infrared 2 (860-1040 nanometers);
Short-wave Infrared 1 (1570-1650 nanometers);
Short-wave Infrared 2 (2080-2350 nanometers); and
Thermal Infrared (10600-12510 nanometers);

Hyperspectral imaging (HSI), like other spectral imaging techniques, is used for collecting and processing information in wavelengths across the electromagnetic spectrum. For example, a hyper spectral camera divides the light range to small sub ranges, such as 300 sub-ranges of 2-nanometer each. HSI is aimed at obtaining a multiplicity of ranges within the spectrum in an image of a scene, usually for detecting objects, identifying materials or states thereof, processes, or the like. In the disclosure below multi spectral cameras and hyper spectral cameras are used interchangeably as long as the device captures at least very-near IR (VNIR), mid-wave IR (MWIR), all or part of the wavelength range of 400 to 1,000 nm and thermal Infrared range.

Whereas the human eye sees color of visible light in mostly three bands (red, green and blue), spectral imaging divides the spectrum into a larger number, covering a wide range of bands, some of which may be beyond the visible spectrum. In hyperspectral imaging, the recorded spectra may have fine wavelength resolution and may cover a wide range of wavelengths. Hyperspectral imaging may measure contiguous spectral bands, as opposed to measuring spaced spectral bands.

Hyperspectral sensors and respective processing systems have applications in a multiplicity of areas. Of special interest are applications in which body parts such as the face of a person are captured by a hyperspectral sensor. Various parameters such as tissue oxygen level, and in particular blood oxygenation level, although invisible to the human eye, are noticeable by HSI.

One technical problem dealt with by the disclosed subject matter is the need to assess the mental state of a driver, and in particular the driver's stress level.

Another technical problem relates to tracking the stress level of the driver, whether during a ride or over a time period such as a day, a month, a year, or the like, and taking an action in accordance with the driver stress level when an acceptable level is exceeded. The action may be aimed at relaxing a driver experiencing high stress level, rewarding relaxed drivers, or the like.

One technical solution comprises the assessment of the stress level of a driver from hyper spectral images of the driver, for example by evaluating physical parameters such as blood oxygenation. This assessment is combined with a second assessment based on telemetry data retrieved from the car systems and providing information about the driving, such as the speed the driver is driving at, lane crossing, acceleration and braking, compliance with road signs and road conditions, or the like. Additional data can be considered in assessing the stress level, for example information obtained by capturing and analyzing the driver's voice using speech to text and natural language processing (NLP), by capturing the driver's face and body and, or analyzing the driver's gestures, accessing and analyzing text or voice messages the driver received the like. Further information can be obtained from external sources, such as a calendar of the driver with or without location data, such that it may be assessed whether the driver is late for a meeting, a Global Positioning System (GPS), weather reports or road conditions report, a wearable device providing indications about the clinical parameters of the driver, a thermometer, or the like.

Another technical solution comprises taking actions in accordance with the stress level. Thus, the stress level should be assessed in real-time, near-real-real-time or at such time intervals that enable actions to be timely taken. Short-range actions may include allowing or preventing control of the car from the user; changing the parameters of alerts given to the driver by the system such as alert level, alert frequency, alert volume or the like; presenting suggestions to the driver, for example to stop for a rest, to get some food or drink wherein the suggestion may be displayed on a dedicated display, on the user's mobile device, or the like; sending a message to a predetermined person, such as a friend of the driver asking them to call the driver and relax him, or the like.

Longer duration actions may include collecting information over time, and using it for determining the premium of the driver for the car insurance, such that a driver that is often stressed may pay a higher premium than a driver who is generally calm.

Yet another technical solution comprises personalizing the parameters for assessing the stress level, such that the stress level is assessed in accordance with the particular driver. For example, a base line blood oxygenation level, a base pulse or other parameters may be determined, such that measured values can be interpreted correctly in respect of the driver.

Yet another technical solution comprises learning and updating the parameters for assessing the stress level over time, such that the stress level is assessed correctly for the particular driver over time.

Yet another technical solution comprises receiving information from a multiplicity of systems as above by a server, and analyzing behaviors of a multiplicity of drivers driving on the same road, at the same time or at different times. The analysis may enable the identification of problematic roads, such that measures can be taken, for example providing rest areas, setting reduced speed limit, or the like.

One technical effect of the disclosure relates to monitoring the mental state of a driver and particularly the stress level of the driver, and taking one or more actions to increase safety for the driver and the people and objects in the vicinity thereof. The actions may include immediate actions, as well as actions intended to reward calm drivers and encourage stressed drivers to relax.

Referring now to FIG. 1, showing a schematic block diagram of an apparatus for assessing a stress level of a driver and taking related actions, in accordance with some embodiments of the disclosure.

The apparatus, generally referenced 100, may be installed in a vehicle such as a car, a bus, or the like. Apparatus 100 may comprise a hyperspectral camera 104. Hyperspectral camera 104 may be installed such that it can capture the face or other exposed body parts of the driver. Hyperspectral camera 104 may be sensitive to very-near IR (VNIR), mid-wave IR (MWIR) and all or parts of the wavelength range of 400 to 1,000 nm and the thermal range.

Apparatus 100 may comprise a vehicle telemetry interface 108 for receiving indications from one or more systems of the car, such as the brakes system, the engine, the cruise controller, or the like. Vehicle telemetry interface 108 may operate by apparatus 100 being connected to a car communication system, such as CANBUS, and communicating with the vehicle systems via such channel.

Apparatus 100 may comprise one or more image capture devices 112, for capturing one or more images or video frames of the driver, of the environment for example the inside of the car, the road including road signs, other vehicles, objects such as other vehicles, pedestrians, road signs, or the like, in the vicinity of the vehicle. Image capture devices 112 may include any visible light camera, such as dashboard camera, which may capture still or visible images.

Apparatus 100 may comprise one or more voice capture devices 116, for capturing the voice of the driver, passengers in the car and optionally external noises.

Apparatus 100 may comprise one or more physical measurement components 120 for taking measurements of physical environmental parameters, such as temperature, humidity, barometric pressure, visibility, or others, or clinical parameters of the driver, such as pulse, blood pressure, temperature or the like.

Apparatus 100 may comprise computing device 124, which may comprise one or more processors 128. Any of processors 128 may be a Central Processing Unit (CPU), a microprocessor, an electronic circuit, an Integrated Circuit (IC) or the like. Alternatively, computing device 124 can be implemented as firmware written for or ported to a specific processor such as digital signal processor (DSP) or microcontrollers, or can be implemented as hardware or configurable hardware such as field programmable gate array (FPGA) or application specific integrated circuit (ASIC). Processor 128 may be utilized to perform computations required by apparatus 100 or any of it subcomponents.

Computing device 124 may comprise one or more storage devices 132 for storing executable components, and which may also contain data during execution of one or more components. Storage device 132 may be persistent or volatile. For example, storage device 132 can be a Flash disk, a Random Access Memory (RAM), a memory chip, an optical storage device such as a CD, a DVD, or a laser disk; a magnetic storage device such as a tape, a hard disk, storage area network (SAN), a network attached storage (NAS), or others; a semiconductor storage device such as Flash device, memory stick, or the like. In some exemplary embodiments, storage device 132 may retain data structures and program code operative to cause any of processors 128 to perform acts associated with any of the steps shown in FIG. 2 below.

The components detailed below may be implemented as one or more sets of interrelated computer instructions, executed for example by any of processors 804 or by another processor. The components may be arranged as one or more executable files, dynamic libraries, static libraries, methods, functions, services, or the like, programmed in any programming language and under any computing environment.

In some exemplary embodiments of the disclosed subject matter, storage device 132 may comprise hyperspectral image analysis engine 136, for analyzing one or more images captured by hyperspectral image 104. Due to the wavelengths captured by hyperspectral image 104, including 400-1000 nanometers and the thermal range, hyperspectral image analysis engine 136 may assess clinical parameters such as but not limited to pigmentations of oxyhemoglobin (HbO2) and deoxyhemoglobin (Hb).

Storage device 132 may comprise physical attribute estimation component 140 for determining physical attributes. One exemplary physical attribute may be the stress level, determined as the ratio between HbO2 and Hb, which defines the oxygen saturation which is indicative of stress. Thus, images obtained by hyperspectral camera 104 can be used for obtaining indications of the stress level.

Storage device 132 may comprise telemetric analysis engine 144 for analyzing the data received by vehicle telemetric interface 108, and determining one or more factors related to stress level by analyzing demonstrated behaviors, such as over speeding, high acceleration and deceleration, lane crossing, or the like.

Analyzing the stress level using a hyper spectral imaging device is disclosed, for example, in "Hyperspectral Imaging for Safety and Security" by Valerie C. Coffey, published in Optics and Photonics News Vol. 26, Issue 10, pp. 26-33 (2015), or in "Detection of Psychological Stress Using a Hyperspectral Imaging Technique" by Tong Chen, Peter Yuen, Mark Richardson, Guangyuan Liu, and Zhishun She, published in IEEE Transactions ON Affective Computing, Vol. 5, No. 4, October-December 2014.

Storage device 132 may comprise image analysis engine 148 for determining one or more parameters from captured images, such as the facial and hand gestures by the driver, outside conditions, or the like.

Storage device 132 may comprise voice analysis engine 152, which may comprise for example speech recognition for recognizing speech by the driver or by the passengers.

Storage device 132 may comprise calendar interface 156, for obtaining information about when and where the driver or another passenger onboard has to be.

Storage device 132 may comprise additional source interface 160, for example interface to a positioning system for determining a current location, interface to the media system of the vehicle or to other information sources.

Data from the above sources may be input into stress level analysis engine 164, which may combine the data into an estimation of the stress level of the driver.

For example, if a sum, a product, an average or another combination of a normalized oxygen saturation level obtained by physical attribute estimation component 140 and normalized stress level as obtained from telemetric analysis engine 144 is below a first threshold, it may be assessed that the driver is relaxed, if the combination exceeds the first threshold and is below a second threshold, then it may be assumed that the driver is somewhat stressed, while if the combination exceeds the second threshold, the driver may be assumed to be stressed.

The combination may also take into account data from the other sources. For example, if it is known from the calendar that the driver has to arrive at a certain time to a certain place, and the GPS indicates that he is running late, the combined stress level may be increased. If image analysis engine 148 indicates excess hand gestures by the driver, or if voice analysis engine 152 indicates loud voices or strong language, the stress level estimation may also be increased.

Once an estimation of the stress level is obtained, it may be provided to action selection engine 168, which may determine one or more actions to be taken in accordance with the estimation. For example, if the driver is extremely stressed, an automatic driving system may take over and not let the driver control the car; an alert system may issue a severe alert to the driver; a message may be sent to a predetermined number to report the stress level of the driver; the stress level may be stored and the accumulated stored reports may be used for determining the insurance premiums, or the like.

Action activation engine 172 may be used for carrying the selected action, such as sending a command to a car system via the communication channel such as the CANBUS, calling or messaging a number, storing a report, or the like.

Storage device 132 may comprise learning engine 176 for learning the parameters of the specific driver, for example stress threshold level, basic saturation level, normal speech volume or the like. Learning may be performed by transmitting the measurements and stress assessments to a server and normalizing the results with other drivers, normalizing clinical parameters of the driver over time, or the like. Learning can also be influenced by feedback, for example the effect of the taken actions on the stress level, e.g., were the actions effective in reducing the stress level. The initial values may be set as general defaults, retrieved from a look up table if some driver characteristics such as gender and age are known, or the like. Receiving information related to a multiplicity of drivers on the same road can also be used for analyzing whether the road is problematic and requires additional surveillance, additional rest areas, or the like, subject for example to an average stress level exceeding a normal level.

The apparatus may be a unit comprising components as detailed above. However, the components may be located in various places over the vehicle, for example, some image and/or voice capture devices may be located at different locations within the car.

Figure 2:
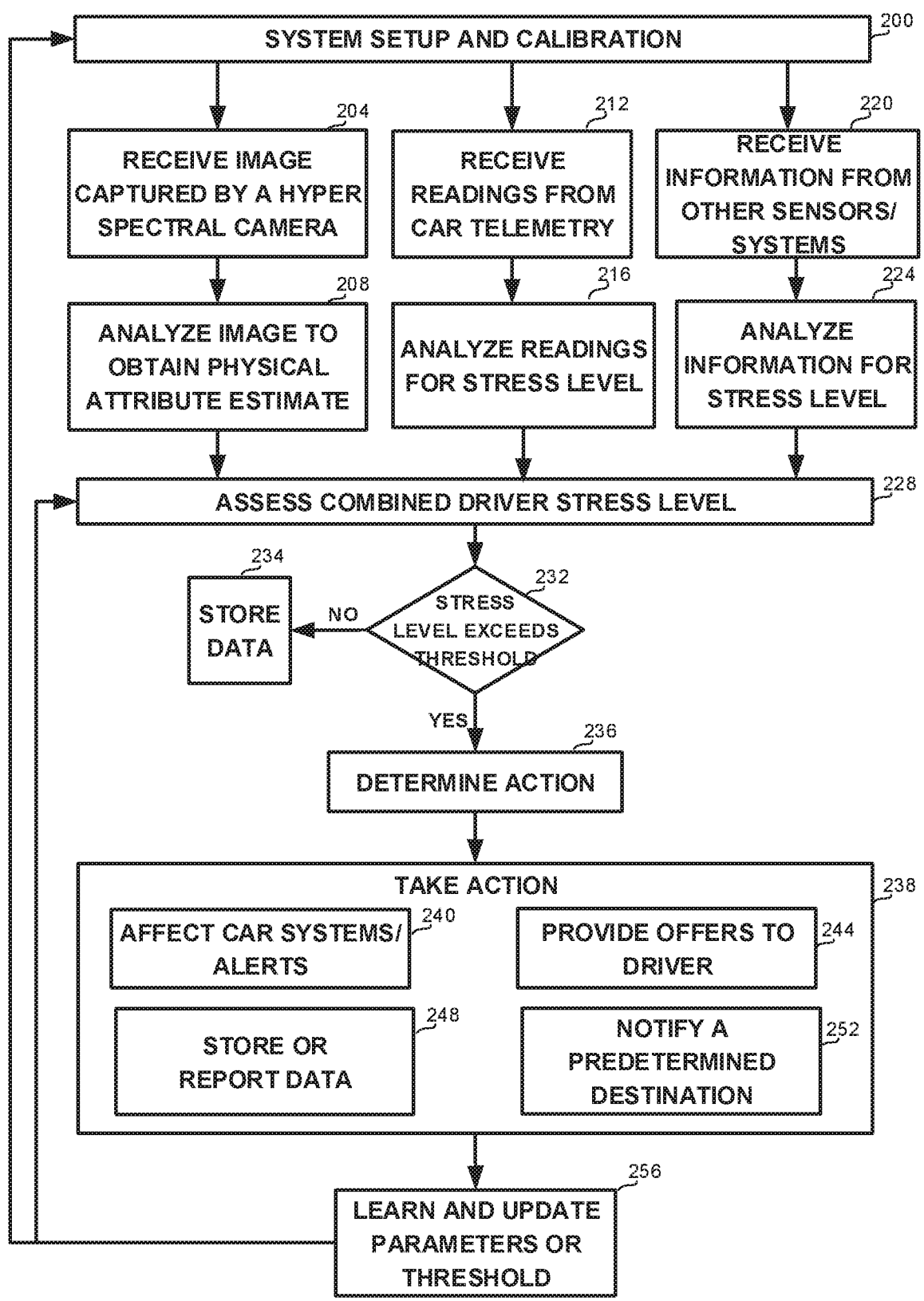
FIG. 2 is a schematic flowchart of a method for assessing and utilizing the assessment of the stress level of a driver, in accordance with some embodiments of the disclosure.

Referring now to FIG. 2, showing a schematic flowchart of a method for assessing a stress level of a driver, in accordance with some embodiments of the disclosure.

On step 200, system setup and calibration may take place. System setup and calibration step 200 can include, for example placing the various capture devices in places where the required image or voice can be captured, for example hyper spectral camera 104 can be located and calibrated such that it captures at least the driver's face and neck.

On step 204, one or more images captured by the hyperspectral camera may be received, and on step 208 the images may be analyzed in order to obtain a physical attribute estimate, such as an estimate to the stress level of the driver.

On step 212, one or more readings may be received from the car telemetry systems, such as speed, acceleration, lane passing, honking, or the like, and on step 216 the stress level may be assessed form the readings. For example, frequent lane passing, frequent honking, a predetermined number of accelerations or decelerations having intensity that exceeds a threshold over a duration, or other factors, may indicate stress.

On step 220, information from other sensors or systems may be received, such as data, readings or capturing. For example, images may be received form one or more image capture devices, audio can be received form a voice capture device, calendar information may be obtained via an interface, location can be obtained from a GPS. or the like. On step 224, the information may be analyzed for stress level indications. For example, high volume speech or excessive hand gestures, being late to a meeting, as deduced from a calendar event and a GPS location, or other events or combinations may indicate high stress levels.

On step 228, an overall assessment of the driver stress level may be obtained by combining at least the stress level as determined on step 208 based on the images taken by the hyper spectral camera and the stress level as obtained on step 216 from the car telemetry. If additional assessments are available, they can also be combined to obtain a possibly more exact assessment. The assessment can also be affected by combination of factors such as driver stress level, and weather as received from a weather report system, or road condition received from a suitable source, and may include actions as detailed above. In other examples the assessment can use a combination of the driver's location and scheduled meeting to realize whether the driver is about to be late and may thus be stressed, analyzing the driver's voice, words, gestures, or the like; analyzing received text or voice messages or the like.

On step 232 it may be determined whether the assessed stress level is below or above a predetermined threshold. It will be appreciated that the threshold can be different for different people, or even change over time for the same driver. Such changing can be periodical for example a different threshold may be applied on different parts of the day, while the change may also be more due to the learning mechanism.

If the stress level does not exceed the threshold, data about the current measurements, received images, and obtained stress levels may be stored in a storage device such as storage device 132.

If the stress level exceeds the threshold, then on step 236 one or more actions to be taken may be determined, such as but not limited to affecting the behavior of car system, such as taking decisions including driving decisions, changing parameters, collecting data, changing control or car alert systems, providing offers to the driver, notifying a predetermined person or system, storing the information, sending a report, or the like.

On step 238 the determined one or more actions can be taken. For example, on step 240 a message may be sent to one or more of the car systems, such as changing the alert level and timing, limiting the speed, enabling or disabling automatic or manual driving, or the like. The message to the car system or to a controller may be sent via a vehicle communication channel, such as CANBUS.

On step 244 one or more offers may be provided to the driver, wither visually on a display device or orally via a speaker, such as offers to stop for food, drink, rest, or the like.

On step 248 the relevant information may be stored as detailed on association with step 234 above, and/or reported to a third party. It will be appreciated that such reporting can but is not required to be immediate. For example, a report about excessive stress level can be reported to the authorities, while data collected over time may be provided to an insurer upon specific request or when the insurance is to be renewed.

On step 252, a predetermined destination may be notified of the stress level, such as a predetermined person who can call the driver.

It will be appreciated that the listed actions are exemplary only, and other actions or combinations may be selected and taken, such as switching on or off the media system, or changing the broadcasted materials.

On step 256, various parameters and thresholds may be adapted, on an immediate or on long term basis, in order to provide better stress level estimation for the particular driver at the particular time. Learning may utilize the effect of previously taken actions in reducing the stress level, the changing of stress level over the day or another time period, the effect pf long drives, or the like.

In some embodiments, too low stress levels may also be identified and alerted, since they may indicate drowsiness or other lack of attention by the driver, The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). Each block may be implemented as a multiplicity of components, while a number of blocks may be implemented as one component. Even further, some components may be located externally to the car, for example some processing may be performed by a remote server being in computer communication with a processing unit within the vehicle. In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method of determining a state of a vehicle driver, to be performed by a device comprising a processor and a memory device, the method comprising:
   receiving by a vehicle telemetry interface, vehicle-related telemetry information from a car telemetry system, wherein the vehicle-related telemetry information comprises at least one of vehicle speed, vehicle acceleration, lane passing and honking;
   assessing by a telemetric analysis engine, a stress level of the driver from the information received from the car telemetry system;
   receiving by an information fusing apparatus, an image of the driver captured by a hyper spectral camera capable of imaging body features invisible to a human;
   analyzing the image by an image analysis engine, to receive at least one indicator to a clinical parameter of the driver;
   learning by a learning engine, stress-related parameters or thresholds from a behavior of the driver over time;
   fusing by a stress level analysis engine, the stress level assessed from the vehicle-related telemetry information received from the car telemetry system, with the at least one indicator received from analyzing the image, and using the stress-related parameters or thresholds as learned to obtain a combined assessment to a stress level of the driver;
   based on the combined assessment, determining an action by an action selection engine; and
   taking the action by an action activation engine, in response to the stress level exceeding a predetermined threshold.

2. The method of claim 1, wherein the action is collecting information to be provided to an insurer or making an offer to the driver.

3. The method of claim 1, further comprising collecting information related to a multiplicity of drivers in a road by an additional source interface, and wherein the action is issuing an alert related to a road, subject to a multiplicity of drivers having stress levels exceeding a threshold.

4. The method of claim 1, wherein learning the stress-related parameters or thresholds comprises:
   transmitting by the information fusing apparatus, the measurements and stress assessments to a server; and
   normalizing by the server, the measurements and stress assessments with other drivers or normalizing measurements of the driver over time.

5. The method of claim 1, wherein the action is affecting a behavior of a car system.

6. The method of claim 5, wherein the car system is an autonomous driving system.

7. The method of claim 5, wherein the behavior relates to changing parameters in accordance with a weather condition and driver behavior.

8. The method of claim 1, further comprising:
   receiving data from an additional source by an additional source interface; and
   analyzing the data to by the stress level analysis engine, obtain an additional indicator; and
   fusing the additional indicator with the telemetry information and the at least one indicator by the stress level analysis engine, to obtain the assessment.

9. The method of claim 8, wherein the additional source is an image capture device or a voice capture device, and further comprising analyzing an image captured by the image capture device or voice captured by the voice capture device.

10. The method of claim 8, wherein the additional source is at least one item selected from the group consisting of: a calendar of the driver, a global positioning system, a weather forecast source, a road condition report and a wearable device.

11. The method of claim 10, further comprising determining by the stress level analysis engine, in accordance with the calendar and with a Global Positioning System whether the driver is late for a meeting.

12. An apparatus for fusing information related to a driver of a vehicle, the apparatus comprising:
   a hyper spectral camera capable of imaging body features invisible to a human;
   car telemetry system providing vehicle-related telemetry information; and
   a processor adapted to perform the steps of:
      receiving vehicle-related telemetry information from a car telemetry system, wherein the vehicle-related telemetry information comprises at least one of vehicle speed, vehicle acceleration, lane passing and honking;
      assessing a stress level of the driver from the vehicle-related telemetry information received from the car telemetry system;
      receiving an image of the driver captured by the hyper spectral camera;
      analyzing the image to receive at least one indicator to a clinical parameter of the driver;
      learning stress-related parameters or thresholds from a behavior of the driver over time;

fusing the stress level assessed from the information received from the car telemetry system, with the at least one indicator received from analyzing the image;

using the stress-related parameters or thresholds as learned to obtain a combined assessment to a stress level of the driver;

based on the combined assessment, determining an action by an action selection engine; and taking the action by an action activation engine, in response to the stress level exceeding a predetermined threshold.

13. The apparatus of claim 12, wherein the action is selected from the group consisting of: affecting a behavior of a car system, collecting information to be provided to an insurer or making an offer to the driver.

14. The apparatus of claim 12, further comprising a connection to a server, wherein the server is adapted to collect information related to a multiplicity of drivers in a road, and issue an alert related to a road, subject to a multiplicity of drivers having stress levels exceeding a threshold.

15. The apparatus of claim 12, wherein for learning the stress-related parameters or thresholds comprises the processor is adapted to:

transmit the measurements and stress assessments to a server; and normalize the measurements and stress assessments with other drivers or normalizing measurements of the driver over time.

16. The apparatus of claim 12, wherein the processor is further adapted to:

receive data from an additional source;

analyze the data to obtain an additional indicator; and fuse the additional indicator with the telemetry information and the at least one indicator to obtain the assessment.

17. The apparatus of claim 16, wherein the additional source is selected from the group consisting of: an image capture device, a voice capture device, a calendar of the driver, a global positioning system, a weather forecast source, a road condition report, and a wearable device.

18. A computer program product comprising a non-transitory computer readable storage medium retaining program instructions configured to cause a processor to perform actions, which program instructions implement:

receiving by a vehicle telemetry interface, vehicle-related telemetry information from a car telemetry system, wherein the vehicle-related telemetry information comprises at least one of vehicle speed, vehicle acceleration, lane passing and honking;

assessing by a telemetric analysis engine, a stress level of the driver from the vehicle-related telemetry information received from the car telemetry system;

receiving by an information fusing apparatus, an image of the driver captured by the hyper spectral camera;

analyzing the image by an image analysis engine, to receive at least one indicator to a clinical parameter of the driver;

learning by a learning engine, stress-related parameters or thresholds from a behavior of the driver over time; and fusing by a stress level analysis engine, the stress level assessed from the information received from the car telemetry system, with the at least one indicator received from analyzing the image;

using the stress-related parameters or thresholds as learned to obtain a combined assessment to a stress level of the driver;

based on the combined assessment, determining an action by an action selection engine; and taking the action by an action activation engine, in response to the stress level exceeding a predetermined threshold.

* * * * *